(12) United States Patent  
Crook

(10) Patent No.: US 6,382,211 B1
(45) Date of Patent: May 7, 2002

(54) SURGICAL RETRACTOR LINER APPLIANCE

(75) Inventor: Berwyn M. Crook, Yardley, PA (US)

(73) Assignee: Medical Creative Technologies, Inc., Colmar, PA (US)

( * ) Notice: Subject to any disclaimer, the term of this patent is extended or adjusted under 35 U.S.C. 154(b) by 0 days.

(21) Appl. No.: 09/463,252

(22) PCT Filed: Jul. 21, 1997

(86) PCT No.: PCT/US97/12800

§ 371 Date: Aug. 21, 2000

§ 102(e) Date: Aug. 21, 2000

(87) PCT Pub. No.: WO99/03416

PCT Pub. Date: Jan. 28, 1999

Related U.S. Application Data

(63) Continuation-in-part of application No. 08/606,606, filed as application No. 05/649,550 on Jul. 22, 1997
(60) Provisional application No. PCT/US97/12800.

(51) Int. Cl.[7] .............................................. A61B 19/00
(52) U.S. Cl. ........................ 128/849; 128/853; 128/856
(58) Field of Search ................................. 128/849–856

(56) References Cited

U.S. PATENT DOCUMENTS

| 1,196,250 A | 6/1916 | Kuhn |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 4,188,945 A | 2/1980 | Wenander ................ 128/132 D |
| 5,159,921 A | 11/1992 | Hoover ......................... 128/20 |
| 5,366,478 A | 11/1994 | Brinkerhoff et al. ......... 660/213 |
| 5,480,410 A | 1/1996 | Cuschieri et al. ............ 606/213 |
| 5,514,133 A | 5/1996 | Golub et al. .................... 606/1 |
| 5,522,791 A | 6/1996 | Leyva .......................... 600/207 |
| 5,524,644 A | 6/1996 | Crook .......................... 128/888 |
| 5,636,645 A | 6/1997 | Ou ............................... 128/898 |
| 5,640,977 A | 6/1997 | Leahy et al. ................. 128/897 |
| 5,649,550 A | 7/1997 | Crook .......................... 128/849 |
| 5,803,921 A | 9/1998 | Bonadio ......................... 606/1 |
| 5,853,395 A | 12/1998 | Crook et al. ................. 604/174 |
| 5,906,577 A | 5/1999 | Beane et al. ................. 600/207 |

Primary Examiner—Michael A. Brown
(74) Attorney, Agent, or Firm—Howson and Howson

(57) ABSTRACT

A surgical retractor liner (12) and integral drape (16) suitable for inserting in an incision and adjusting in place to prevent cross-contamination during surgery between the incised cavity and the surrounding skin of the patient. In one embodiment, a flexible elastic liner (12) impervious to microorganisms has resilient inner (20) and outer rings (18) at either end for holding the liner (12) firmly in the incision. The outer ring (18) is rolled down over itself drawing the liner (12) taut and contiguous in the incision. In another embodiment a skirt (14) is sealingly joined at the outer ring (18) and tapers outwardly and sealingly joins to a drape (16) around a central aperture (16a) therein. The inner ring (20) is inserted and expanded against the inner edge of the incision, and the outer ring (18) is rolled down over the liner (12) and skirt (14) to draw the liner (12) taut in the incision and to retract the sides of the incision while positively anchoring the drape (16) in place around the area of the incision. In another embodiment, a lengthwise incrementally and automatically adjustable wound protector and retractor is provided.

10 Claims, 3 Drawing Sheets

SURGICAL RETRACTOR LINER APPLIANCE

CROSS-REFERENCE TO RELATED APPLICATIONS

This is a 371 of PCT/US97/12800, filed Jul. 21, 1997. The subject matter of this application is a c-i-p to U.S. patent application No. 08/606,606, filed Feb. 26, 1996, now U.S. Pat. No. 5,649,550, granted Jul. 22, 1997.

FIELD OF THE INVENTION

The present invention relates generally to improvements in surgical devices, and more particularly to an improved adjustable retractor, and a retractor with a liner and integral drape therefor for preventing contamination of incised cavity walls of various thicknesses during surgery.

BACKGROUND OF THE INVENTION

The sides of an open incision, as well as matter such as body parts and fluids passing through the incision during surgery, are inherently susceptible to cross-contamination by infectious microorganisms or like matter. Therefore, extreme care is required to insure that any exposed fluids or tissues are completely isolated from each other.

Various designs have been proposed and utilized to prevent transmission of indigenous and exogenous contaminants to healthy viscera from infectious tissues or fluids. U.S. Pat. No. 5,524,644 by Berwyn M. Crook, filed Jun. 9, 1995, describes an incision liner and retractor device which can be installed in an incision, incrementally adjusted in place to form-fit a wide range of cavity wall thicknesses, and retract the sides of the incision apart for better access to the abdominal cavity. It employs a flexible impermeable liner of pliable plastic material with opposite ends terminating at inner and outer resilient O-rings. The inner O-ring is inserted in the cavity by squeezing it through the incision and allowing it to expand around the inner edge of the incision. The outer O-ring is then rolled down over the portion of the liner extending out of the incision until it is tight against the outer rim of the incision and the remaining portion is drawn taut and contiguous with the incision sides. The outer O-ring is generally oblong in cross-section to provide a positive gripping surface for the fingers to roll the outer O-ring more easily, especially when the liner or the surgeon's gloves are slippery.

In many instances, a surgical drape may be first placed over the patient's body before the incision liner and retractor device is installed. This combination further reduces the risk of cross-contamination between the open cavity and the skin around the incision, especially if an organ is brought outside the abdominal cavity to perform surgery on it. However, since the liner and drape are not integrally connected, there is no assurance that the drape may not slide from beneath the outer O-ring and leave the patient's skin exposed in a most vulnerable region immediately adjacent to the incision.

Some prior art surgical protectors address this problem to a limited degree. For instance, U.S. Pat. No. 3,397,692 to Creager, Jr. et al. discloses an incised surgical device in which a resilient ring cemented around the rim of a central aperture in a drape is squeezed together and expanded in the cavity to grip the incised edge of the peritoneum. The drape is bunched together where it passes through the incision and then spreads out over the body surface in radially diminishing wrinkles. U.S. Pat. No. 4,188,945 to Wenander similarly provides a surgical cloth with a semi-rigid thread hemmed in around a central aperture. A portion of the cloth around the aperture is gathered together and inserted in an incision, and then enlarged under the incision edge by increasing the length of thread around the aperture. Like the surgical device of Creager, Jr. et al., a wrinkled surface is created in the incision and around the operating site. Consequently, neither device provides a relatively smooth surface in the incision and around the wound where extracted viscera may be placed nor positive retraction of the sides of the incision. In addition, there is no means for preventing external portions of the drape from slipping in and out of the incision with movement of the surgeon's hand.

OBJECTS OF THE INVENTION

Accordingly, it is an object of the present invention to provide an improved surgical retractor liner and integral drape which prevent exposure to cross-contamination by infectious fluids and solids between an incised cavity and the skin around the incision.

Another object of the invention is to provide a surgical retractor liner and integral drape assembly which interfaces smoothly and contiguously with the sides of an incision and with the skin around the incision.

Still another object of the invention is to provide a retractor liner with integral drape which can be easily installed and adjusted in place to fit a wide range of cavity wall thicknesses.

A further object is to provide a retractor liner which will positively insulate an incision from exposure to indigenous and exogenous contaminants and positively retract the sides of the incision for a wider opening to the cavity.

A further object of the present invention to provide a relatively low cost surgical retractor liner of simplified design which can be easily installed in a wound and adjusted in place to form fit a wide range of cavity wall thicknesses for protection against harmful contaminants.

SUMMARY OF THE INVENTION

These and other objects and aspects of the invention are accomplished in one embodiment by a surgical retractor liner and integral drape which can be inserted in an incision and incrementally adjusted tightly in place in the cavity wall and on the surrounding skin to prevent cross-contamination with body fluids and solids during surgery. It includes a flexible plastic film retractor liner impervious to microorganisms with opposite ends terminating at inner and outer resilient O-rings. The inner O-ring is installed in the incision by squeezing opposite sides together, inserting it through the incision and allowing it to expand around the inner, edge of the incision. The length of the retractor liner is selected to allow a portion to extend out of the incision for rolling down until it is tight against the outer edge of the incision and retracts the sides of the incision for widening the opening. A flexible plastic film skirt fixed at one end around the outer O-ring, and coaxial with the retractor liner, tapers outwardly toward the inner O-ring with the other end sealingly joining the rim of a centrally located aperture in a flexible drape. The extended length of the skirt is at least as long as the portion of the retractor liner fully extending out of the incision when the inner O-ring is expanded against the inner edge. This assures that the drape completely adheres to the surface around the incision and remains fixed in place by the retractor liner and by adhesive patches fixed to the drape. The size of the drape is sufficient to cover the area around the operating site and to prevent it from exposure to any contaminating fluids and tissue.

In another embodiment, the retractor liner comprises a flexible liner of thin substantially elastic material, separate from the drape, secured at opposite open ends around resilient inner and outer O-rings.

In both embodiments, the outer O-ring in cross-section is generally circular with opposed flat sides in planes generally transverse to the extended length of the liner for restoring the outer O-ring to its preformed configuration when turned about the circumferential axis of rotation of the ring. The flat sides also provide gripping surfaces for manually turning the outer O-ring with greater ease, especially when the liner or the surgeon's gloves are slippery. The retractor liner may be constructed in a single liner length with different circumferences for accommodating a wide range of incision sizes and cavity wall thicknesses.

BRIEF DESCRIPTION OF THE DRAWINGS

The foregoing and other objects, features, and advantages of the invention will become more apparent from the following description of the preferred embodiments when taken in conjunction with the accompanying drawings wherein.

DESCRIPTION OF THE PREFERRED EMBODIMENTS

Figure 1:
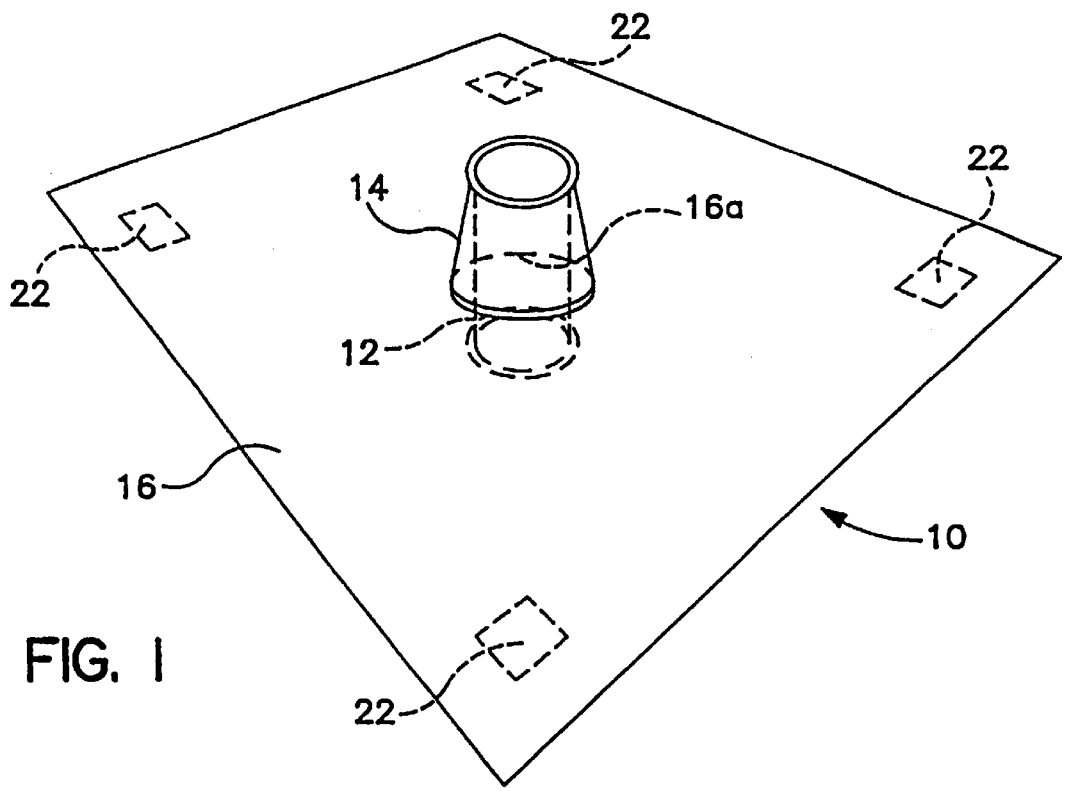
FIG. 1 represents a perspective top view of one embodiment of a surgical retractor liner and integral drape device according to the invention.

Referring now to the drawings wherein like reference characters designate like or corresponding parts throughout the several views, there is shown in FIG. 1 a surgical retractor liner and integral drape device 10 comprising an incision retractor liner 12 of uniform circumference along its length coaxially extending through a skirt 14 and a central aperture 16a in a drape 16.

Figure 2:
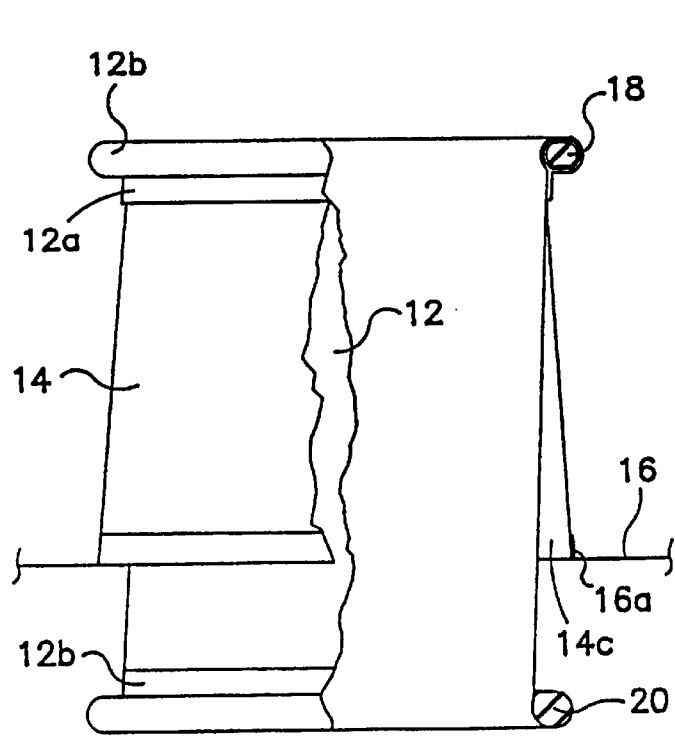
FIG. 2 is a side view partially in cross-section of a portion of the embodiment of FIG. 1.
Figure 3:
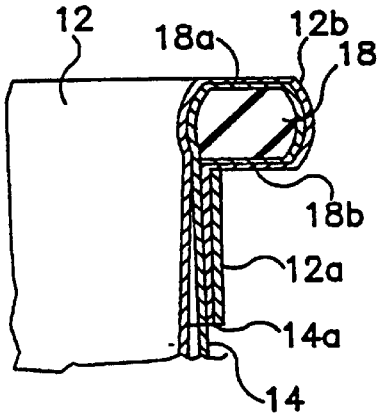
FIG. 3 is an enlargement in cross section of an upper portion of the embodiment shown in FIGS. 1 and 2.

As best seen in FIG. 2, retractor liner 12 and skirt 14 have adjacent upper ends which wrap around an outer O-ring 18 and overlap at annular edges 12a and 14a (FIG. 3) and seal to each other and to the outer side skirt 14. A lower end portion of retractor liner 12 wraps around an inner O-ring 20 and overlaps at an annular edge 12b and seals to the outer side of retractor liner 12; whereas a lower end of skirt 14 is sealed around the perimeter of aperture 16a. Retractor liner 12 is essentially uniform in circumference along a central longitudinal axis defined by the extended length of the liner. Skirt 14 is coaxial with retractor liner 12 and tapers outwardly to aperture 16a.

Outer O-ring 18 is generally oblate in cross-section with opposed upper and lower flat chordal sides 18a and 18b substantially normal to the extended length of retractor liner 12. Sides 18a and 18b are located equidistant from, and on opposite sides of, the centroid of the radial cross-section through O-ring 18. The oblate shape provides an over-center snap action when O-ring 18 is rolled about itself onto retractor liner 12 and skirt 14 for incrementally shortening the upper ends and for resisting unrolling after being shortened.

Inner O-ring 20 is entirely circular in cross-section, but may have a similar cross-section as O-ring 18 for incrementally shortening the lower end of retractor liner 12.

Figure 4:
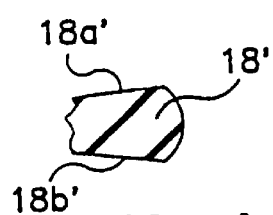
FIG. 4 is a view in radial cross section of an alternate embodiment of an O-ring for use in the upper portion of the assembly shown in FIG. 3.

FIG. 4 illustrates in radial cross-section an alternate embodiment of an outer O-ring 18'. The upper and lower sides 18a' and 18b' taper outwardly from opposite sides of a plane normal to the extended length of liner 12 thereby allowing O-ring 18' to be turned with less resistance around its annular axis due to the lesser mass near the inner circumference O-ring 18'. This structure is particularly desirable for large diameter rings having relatively large diameter cross-sections.

The materials for making assembly 10 are selected to insure stability when installed. One preferred material for retractor liner 12, skirt 14 and drape 16 is a substantially inelastic heat-sealable 3-mil polyolefin plastic film, such as Saranex™ film 2050 by The Dow Chemical Company. Another preferred material for liner 12 and skirt 14 is a substantially elastic heat-sealable 2-mil polyurethane film, such as Dureflex® PT6100S by Deerfield Urethane, Inc.

The polyurethane material has been found to provide certain advantages not available with the Saranex™ polyolefin material. For instance, the elastic polyurethane material takes up any lengthwise adjustment which cannot be fully accommodated by the incremental adjustments made by rolling the O-ring 18'. In addition, the elastic polyurethane provides a better retraction function along the edges of the incised wound. This is believed due, at least in part, to the better wound edge margin gripping action resulting from the axial take-up of the elastic polyurethane.

The difference between the non-elastic polyolefin material and the elastic polyurethane may be seen from a test wherein five 1"×3" specimens of each of these materials were stretch tested at room temperature (+75° F.) and permanent deformation (deflection) calculated from its load vs. displacement curve. The average deflection of the polyolefin film was approximately 0.354 inch/inch, while the polyurethane specimen deflection averaged approximately 0.167 inch/inch.

O-rings 18 and 20 are preferably preformed of an elastomeric medical-grade polyurethane of sufficient hardness to retain the rings expanded in place around the inner and outer rims of the incision. The O-ring material must be compliant enough to allow the fingers to turn the outer O-ring 18 over 180° around its annular axis from the preformed configuration. They may be color-coded with different colors, such as white and blue, for easier recognition of the correct O-ring to be inserted in an incision.

Drape 16 may be adhered directly to the skin of the patient or to an underlying drape by an adhesive spread over the underside of the drape, or by adhesive patches 22 at selected locations on the underside of the drape. The size of drape 16 is selected to provide effective protection from exposure to infectious fluids and tissue in the vicinity of the incision.

The length of a fully extended retractor liner 12 is typically around 150 mm to accommodate most wall thicknesses at the incision. An assortment of liner and O-ring diameters are provided to accommodate different lengths of incisions, and the personal preference of the surgeon. U.S. Pat. No. 5,524,644, supra, discloses a table of liner and O-ring diameters available for different incision lengths, and its disclosure is incorporated by reference herein. The urethane O-rings are typically in the range of 50–90 Shore A durometers.

The diameter of an upper length of skirt 14, in a relaxed state before stretching around O-ring 18 and sealing it at edge 14a, corresponds substantially to the diameter of retractor liner 12. The remaining lower portion tapers outwardly to the diameter of aperture 16a which is slightly larger than the diameter of retractor liner 12 to allow clearance for retractor liner 12 to be stretched into contact with the outer rim of the incision. The length of skirt 14 must not be shorter than retractor liner 12 by an amount greater than the thickness of the wall at the incision. If the difference were greater, the drape will not adhere completely to the skin immediately adjacent to the incision. Of course, if the difference is less than the wall thickness, the lower end of skirt 14 will merely bunch up around the uninserted portion of retractor liner 12 and roll onto O-ring 18 but still provide a satisfactory seal. Typically, the thickness of abdominal walls ranges between 25 mm and 75 mm. Therefore, for an overall liner length of 150 mm, an effective skirt length should not be shorter by more than 25 mm, namely an overall length of 135 mm.

Figure 5A:
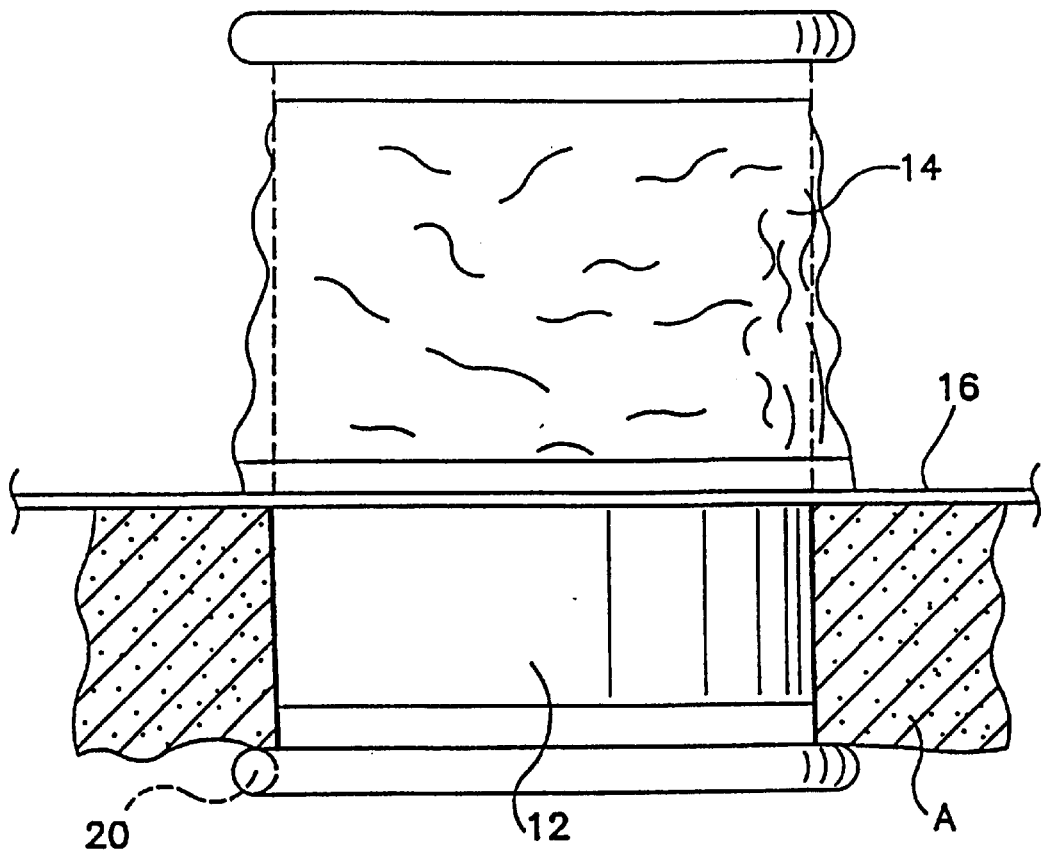
FIGS. 5A and 5B are schematic illustrations of the device in two stages of installation in an incision.
Figure 5B:
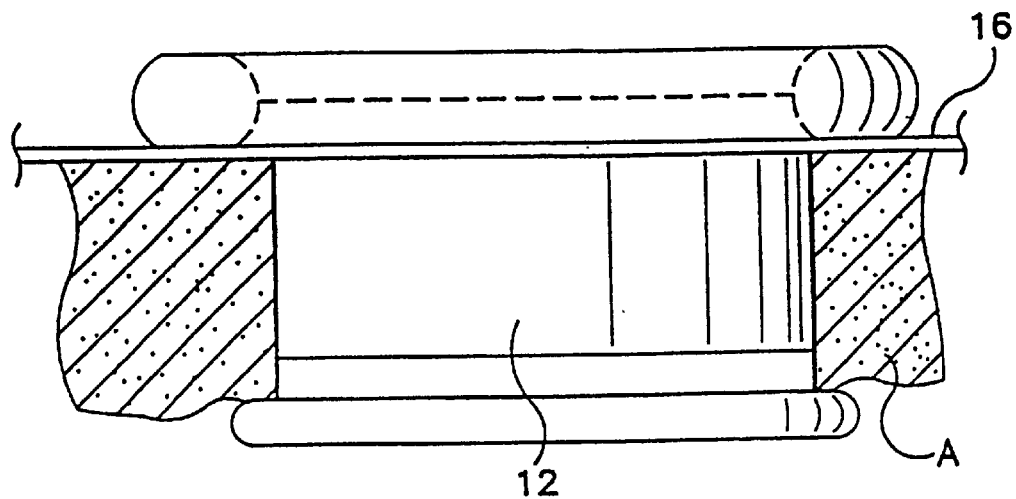

A typical installation of the retractor liner and integral drape assembly 10 is illustrated in two stages in FIGS. 5A and 5B. In FIG. 5a, retractor liner 12 is inserted into an incision in the abdominal wall A with the inner O-ring 20 expanded against the inner rim of the incision and drape 16 adhered to the skin, or to an underlying drape not shown. In this installation skirt 14 is shorter than retractor liner 12 by a difference slightly less than the thickness of the abdomen wall, thereby causing skirt 14 to bunch up around fully extended retractor liner 12. In FIG. 5B, the upper end of the assembly containing O-ring 18 is rolled down over the outside of skirt 14, abuts the top of drape 16 with skirt 14 drawn taut against the incision, and retracts the sides of the incision to widen the opening. Drape 16 is thusly positively anchored against slipping out from under the rolled down portions of liner 12 and skirt 14.

Figure 6:
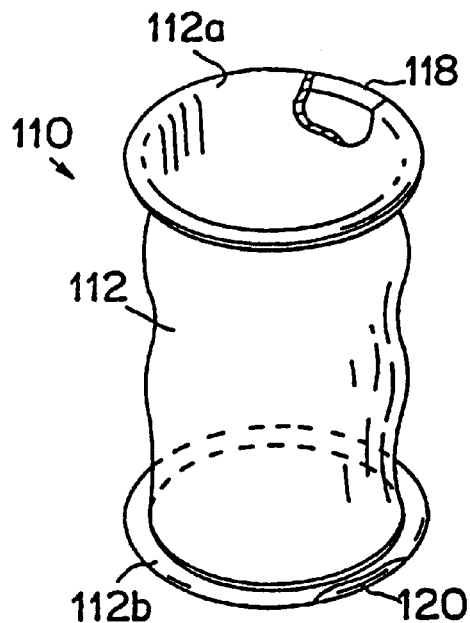
FIG. 6 is an isometric view of another embodiment of a retractor liner according to the invention, in a fully extended state and with portions cut away.

Referring now to FIG. 6, an adjustable retractor device 110 includes a thin relatively elastic liner 112, uniform circumference along its length and impervious to solids and fluids containing bacteria and other harmful contaminants.

Figure 7:
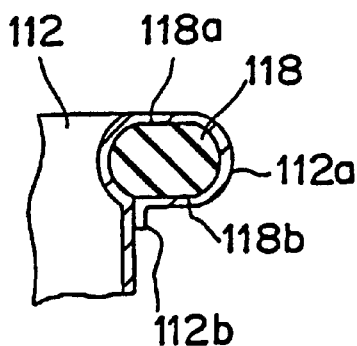
FIG. 7 is a view in longitudinal cross-section of an outer end of the retractor liner of FIG. 6.

As best seen in FIG. 7, the upper end portion 112a of the liner 112 wraps around outer O-ring 118 and terminates in an annular edge portion 112c sealed around the outer side of liner 112. At least one O-ring, such as the O-ring 118, is generally oblate in cross-section having opposed flat chordal side surfaces 118a and 118b which are transverse, i.e. substantially normal, to the liner central longitudinal axis defined by the extended length of liner 112, as shown in FIGS. 6–8b. As shown, the chordal surfaces 118a and 118b are located equidistant from, and on opposite sides of, the centroid of the cross-section. The surfaces 118a and 118b provide surface means for purposes to be described.

Inner O-ring 120 is secured to lower end portion 112b in the same manner as O-ring 118, except the configuration in cross section is entirely circular. If desired, both O-rings may have the same cross-sectional shape as O-ring 118 to provide reversibility to the retractor liner device 110.

The oblate shape of the O-ring 118 provides stability in a plane perpendicular to the longitudinal axis of the liner 112 and provides an over center snap action when rolled about itself and the liner, thereby providing incremental shortening in predetermined increments and resistance to lengthening after shortening.

The materials and dimensions of adjustable surgical device 10 are selected to ensure stability when installed. A preferred elastic material suitable for liner 112 is a 2-mil polyurethane film, such as Dureflex® PT61005 supra. It is produced in seamless tubular form or by a flat sheet in a cylindrical form with the meeting margins along the side overlapped and sealed. A nominal liner length suitable for minimally invasive surgery is typically around 150 mm. Liner diameters will vary according to wound length as will be discussed.

Outer and inner O-rings 118 and 120 are preferably preformed of an elastomeric medical grade material of sufficient hardness to retain O-rings 118 and 120 expanded in place around the inner and outer edges of the wound. Like O-ring 18, the material must be compliant enough to allow O-ring 118 to be turned by the fingers over 180 degrees around its annular axis from the preformed configuration. Urethane is therefore the preferred elastomeric material. When the O-rings are of different configurations, the O-rings are preferably color-coded with different colors, such as white and blue, for aiding in recognizing the correct end of the protector to be inserted in the wound.

The inside circumferences of O-rings 118 and 120 generally correspond to the outside circumference of liner 112. By way of example, a urethane O-ring 118 for use with a liner 110 mm (4.33 inches) in diameter has a diameter across the transverse cross section of about 7.94 mm (5/16 inch) with a distance between parallel flat sides 118a and 118b of approximately 6.10 mm (0.240 inch). O-ring 120 has a diameter of its circular cross-section of about 7.94 mm (5/16 inch). Of course, the sizes of the O-rings and liners will vary according to wound size and wound wall thickness, and the personal preference of the surgeon will affect the choice of size for a particular surgical procedure.

The following table sets forth a preferred relation between incision length and liner and O-ring and liner diameters. It also sets forth the preferred cross-sectional diameters for each O-ring, it being understood that O-ring 18 has opposed flats and is, therefore, oblate and not circular in cross-section.

| Incision Length (mm) | Liner Diameter (mm) | O-Ring Cross Sectional Diameter (mm) |
| --- | --- | --- |
| 10 | 30 | 5.15 |
| 20 | 30 | 5.15 |
| 30 | 60 | 7.13 |
| 40 | 60 | 7.13 |
| 50 | 80 | 7.52 |
| 60 | 80 | 7.52 |
| 70 | 110 | 7.92 |
| 80 | 110 | 7.92 |
| 90 | 110 | 7.94 |
| 100 | 130 | 9.53 |
| 110 | 130 | 9.53 |
| 120 | 150 | 11.11 |
| 130 | 150 | 11.11 |
| 140 | 170 | 12.70 |
| 150 | 170 | 12.70 |

-continued

| Incision Length (mm) | Liner Diameter (mm) | O-Ring Cross Sectional Diameter (mm) |
| --- | --- | --- |
| 160 | 190 | 14.29 |
| 170 | 190 | 14.29 |
| 180 | 210 | 15.88 |
| 190 | 210 | 15.88 |
| 200 | 230 | 15.88 |

The durometers of the O-rings set forth in the above table should be in a range of 50 to 90 Shore A. The preferred material is urethane, but silicone could be used with some loss of stability after installation and adjustment. The best stability is achieved by using a material having a high modulus of elasticity with a ring, as manufactured, having a minimum of residual stresses and strains. The size of the flats affects both gripability for adjustment and stability after adjustment, since the larger the size of flats for a given O-ring cross-sectional diameter, the less stability that exists. By way of example, a preferred flat width for an O-ring having a cross-sectional diameter of 7.94 mm (5/16 inch) is 6.10 mm (0.240 inches). It is expected that with increasing diameters each flat width should increase proportionately based on a formula: W=xD where W is the width of the flat; D is the diametrical cross-section of the O-ring; and x is a constant equal to 0.85 for a urethane ring having a hardness within the ranges stated.

Figure 8A:
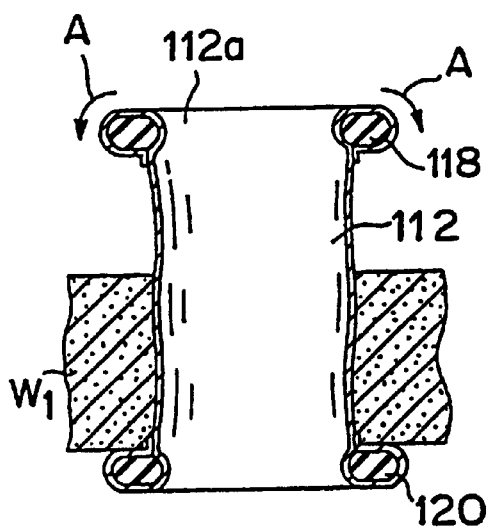
FIGS. 8A is a schematic representation in longitudinal cross-section of the retractor liner of FIG. 6 partially installed in a surgical wound.
Figure 8B:
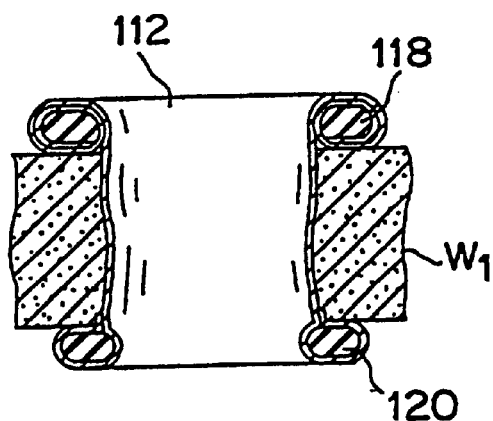
FIG. 8B schematically illustrates the retractor liner of FIG. 6 in two stages of installation in an incision.

In using the adjustable surgical device in a minimally invasive abdominal surgical procedure, the abdomen is routinely prepared with antiseptics and dried; the site for the incision is traced on the abdomen and covered with a surgical drape; and a muscle-split is made at the site through the peritoneum. As illustrated in FIGS. 8A and 8B, retractor and liner 110 is placed in wound $W_1$ by squeezing inner O-ring 120 into a tight oblong shape and inserting it lengthwise through the incision and letting it expand inside the peritoneum around the inner edge of the wound. Outer end portion 112a is gripped by the thumb and fingers at flat sides 118a and 118b of outer ring 18 (FIG. 7) and turned outwardly, in opposite directions shown by arrows A, rolling liner 112 on the O-ring until it abuts the outer edge of the wound $W_1$ as shown in FIG. 8B. However, as a result of the elasticity of the liner material, any lengthwise adjustment not accommodated by the incremental adjustments causes the part of liner 112 in the wound between O-rings 118 and 120 to be thereby drawn into contiguous contact with the edge margins of wound $W_1$ and hence with the wound walls to provide a self-retaining protective barrier during surgery which is impervious to contaminating solids and fluids. If desired, the protector 10 can also be pre-adjusted prior to insertion, or partially pre-adjusted.

Some of the many advantages and novel features of the invention should now be readilapparent. For example, the invention provides an improved liner and drape device which prevents exposure between an incised cavity and the skin around the incision to cross-contamination by infectious fluids and tissue. The assembly is positively anchored in place around the operating site by the installed liner, smoothly interfaces against the sides of the incision and the surrounding skin, and retracts the sides of the incision for a wider opening. It can be easily installed in an incision and adjusted in place to fit a wide range of cavity wall thicknesses as well as provide positive insulation of an incision and surrounding skin from indigenous and exogenous contaminants.

A relatively simple and inexpensive surgical retractor liner is provided for protecting wounds from exposure to contamination. It can be quickly and easily installed in a wound and adjusted in place to form-fit a wide range of cavity wall thicknesses, and it stays in place after insertion. A fewer number of combinations of sizes of protectors are needed to accommodate a variety of incision sizes and cavity wall thicknesses.

Of course, it will be understood that various changes in the details, materials, steps and arrangement of parts, which have been herein described and illustrated in order to explain the nature of the invention, may be made by those skilled in the art within the principle and scope of the invention as expressed in the appended claims.

What is claimed is:

1. An incrementally and automatically adjustable surgical device (110) comprising:

an elongate liner (112) of elastomeric material open at opposed ends;

a first resilient ring (120) secured around one of said ends (112b) deformable into an oblong shape for insertion with a portion of said liner (112) into a wound and formed to expand against the inner edge of the wound; and a second resilient ring (118) secured around the other of said liner ends (112a) and formed with an oblate cross-section having opposed chordal surfaces (118a, 118b) for enabling the gripping and rolling of a remaining portion of said liner (112) in increments on itself and against the outer edge of the wound, whereby the liner length may be adjusted in increments before placement in the wound and automatically adjustable lengthwise after placement.

2. An adjustable surgical device (110) according to claim 1 wherein said elastic material has a deformation of approximately 0.167 inch/inch.

3. An adjustable surgical device (110) according to claim 1 wherein:

said chordal surfaces (118a, 118b) are disposed transverse to the length of said liner (112) in both an as-manufactured condition and an incrementally-adjusted condition.

4. An adjustable surgical device (110) according to claim 3 wherein:

said chordal surfaces (118a, 118b) are flat and are located in parallel planes equidistant from the centroid of said cross-section.

5. An adjustable surgical device (110) according to claim 4 wherein:

said parallel planes are perpendicular to the central longitudinal axis of the liner (112).

6. An adjustable surgical device (110) according to claim 4 wherein:

said liner (112) is a thin sheet of generally cylindrical form wrapped about said rings (118, 120) and secured thereto.

7. An adjustable surgical device (110) according to claim 1 wherein:

each of said rings (118, 120) is of urethane having a hardness in a range of about 50 to about 90 Shore A scale.

8. A lengthwise adjustable surgical device (110) for use in surgery comprising:

an elongate elastomeric liner (112) open at opposite ends;

an inner ring (120) secured to said liner (112) at one end (112b), an outer ring (118) secured to said liner (112) at the opposite end (112a), said outer ring (118) having an oblate transverse cross-section defined by a diametrically opposed pair of arcuate surfaces interconnected by an opposed pair of chordal surfaces (118a, 118b), said chordal surfaces (118a, 118b) extending outwardly from said liner (112) in a plane perpendicular to a central axis extending lengthwise of said liner (112), said outer ring (118) being in a minimally strained stable condition when said chordal surfaces (118a, 118b) are lying in said plane, said outer ring (118) being operable, when rolled 180° about its centroid, to roll said liner (112) about itself and thereby to adjust the length of the liner (112) in increments.

9. A lengthwise adjustable surgical device (110) according to claim 8 wherein at least said outer ring (118) is of urethane having a durometer in a range of about 50 to about 90 Shore A.

10. A lengthwise adjustable surgical device (110) according to claim 8 wherein the chordal width of each chordal surface (118a, 118b) is defined substantially by the formula:

W=xD, wherein W is the width, x is a constant of 0.85, and D is the diametrical distance between said arcuate surfaces.

* * * * *

UNITED STATES PATENT AND TRADEMARK OFFICE
CERTIFICATE OF CORRECTION

PATENT NO.    : 6,382,211 B1
DATED         : May 7, 2002
INVENTOR(S)   : Crook

It is certified that error appears in the above-identified patent and that said Letters Patent is hereby corrected as shown below:

<u>Title page,</u>
Related U.S. Application Data, replace: "[63] Continuation-in-part of application No. 08/606,606, filed as application No. 05/649,550 on Jul. 22, 1997" with -- [63] Continuation-in-part of application No. 08/606,606, filed on Feb. 26, 1996 issued as U.S. Patent No. 5,649,550 on July 22, 1997 --; and delete:
"[60] Provisional application No. PCT/US97/12800."

Signed and Sealed this

First Day of October, 2002

*Attest:*

*Attesting Officer*

JAMES E. ROGAN
*Director of the United States Patent and Trademark Office*